United States Patent
Werenicz et al.

[11] Patent Number: 5,827,252
[45] Date of Patent: Oct. 27, 1998

[54] METHOD FOR PRODUCING A CONTINUOUS THERMOPLASTIC COATING AND ARTICLES CONSTRUCTED THEREFROM

[75] Inventors: Harald Werenicz, Reppenstedt; Thomas Wittkopf, Adendort; Gerhard Voss, Lüneburg; Peter Remmers, Hamburg, all of Germany; Mark G. Katsaros, Mahtomedi, Minn.; Robert Gordon Polance, Vadnais Heights, Minn.; Mark S. Kroll, Arden Hills, Minn.

[73] Assignee: H.B. Fuller Licensing & Financing, Inc., St. Paul, Minn.

[21] Appl. No.: 705,578

[22] Filed: Aug. 29, 1996

Related U.S. Application Data

[63] Continuation of PCT/EP96/00377 Jan. 30, 1996.

[30] Foreign Application Priority Data

Feb. 23, 1995 [WO] WIPO ............... PCT/EP95/00665

[51] Int. Cl.$^6$ ........................................... A61F 13/15
[52] U.S. Cl. ......................................................... 604/367
[58] Field of Search .................................. 604/366, 367, 604/385.1

[56] References Cited

U.S. PATENT DOCUMENTS

| | | |
|---|---|---|
| 4,627,847 | 12/1986 | Puletti et al. . |
| 4,692,161 | 9/1987 | Puletti et al. . |
| 5,009,652 | 4/1991 | Morgan et al. ................ 604/385.1 |
| 5,422,172 | 6/1995 | Wu . |
| 5,549,775 | 8/1996 | Odorzynski ................... 604/385.1 |
| 5,558,658 | 9/1996 | Menard et al. ................ 604/385.1 |

FOREIGN PATENT DOCUMENTS

| | | |
|---|---|---|
| 0 187 728 A2 | 7/1986 | European Pat. Off. . |
| 0 189 911 A3 | 8/1986 | European Pat. Off. . |
| 0 508 485 A1 | 10/1992 | European Pat. Off. . |
| 96322880 | 6/1995 | Japan . |
| 96323930 | 3/1997 | Japan . |
| WO 96/26697 | 9/1996 | WIPO . |

*Primary Examiner*—Robert A. Clarke
*Attorney, Agent, or Firm*—Nancy N. Quan; Carolyn A. Fischer

[57] ABSTRACT

This invention relates to a non-contact coating method for producing a continuous coating and articles constructed therefrom. This invention further relates to a method for producing a textile material with a moisture-impermeable barrier layer and to a method for producing a moisture-absorbing article of hygiene which has such a barrier layer. This invention particularly relates to a textile material and hygienic disposable articles comprising a body fluid impermeable barrier layer produced from said coating method. Preferably, the thermoplastic composition used in the method for producing the barrier layer exhibits certain rheological characteristics.

20 Claims, 1 Drawing Sheet

METHOD FOR PRODUCING A CONTINUOUS THERMOPLASTIC COATING AND ARTICLES CONSTRUCTED THEREFROM

REFERENCES TO RELATED APPLICATIONS

This application is a continuation-in-part of application Ser. No. PCT/EP96/00377, filed Jan. 30, 1996 which claims priority from PCT/EP95/00665, filed Feb. 23, 1995, abandoned.

FIELD OF THE INVENTION

This invention relates to a non-contact coating method for producing a continuous coating and articles constructed therefrom. This invention further relates to a method for producing a textile material with a moisture-impermeable barrier layer and to a method for producing a moisture-absorbing article of hygiene which has such a barrier layer. This invention particularly relates to a textile material and hygienic disposable articles comprising a body fluid impermeable barrier layer which can be produced from said coating method. Preferably, the thermoplastic composition used in the coating method for producing the barrier layer exhibits certain rheological characteristics.

BACKGROUND OF THE INVENTION

For various applications, materials are required which are impermeable to liquids such as water and body fluids, but at the same time have a textile character which is as close as possible to materials without the impermeability characteristics. One example of such application is hygienic articles such as disposable diapers, feminine napkins, panty liners, surgical drapes, bed pads, and the like. Such hygienic articles often have a substantial absorption capacity. To ensure that the liquid which is to be absorbed does not reach articles of clothing, such hygienic articles customarily have a continuous layer of a body fluid impermeable film on their garment facing side. Since touching this film material is an unwelcome sensation for a number of users, it has been suggested to cover the outward side of the film with a thin layer of textile material so that the article has a textile feel also on its exterior surface.

EP-A-O 187 728 teaches a disposable diaper with a barrier layer in the form of a plastics material film, typically consisting of a polyolefin, a polyacrylate, of PVC, nylon or other thermoplastic material. The barrier film is laminated, adhered or welded onto a thin nonwoven layer, which makes it necessary to prepare the film laminate off-line. As an alternative, it is suggested that the plastics material of the film is to be extrusion coated onto the nonwoven. The laminate, thus formed, is then used as the outermost material layer in such a way that the film layer is on the inside, so that the outer nonwoven layer provides the desired exterior texture. This production method is rather expensive. High molecular weight plastic materials such as polyethylene, polypropylene, polyacrylate and so on, have low melt flow indices and can (if at all) only be processed into impermeable films on very sophisticated machinery. This would also be true for the suggested direct extrusion coating which does not appear to have been reduced to practice yet. Separately producing the film, with subsequent laminating onto the nonwoven, is even more inefficacious in view of the additional production step required.

U.S. Pat. Nos. 4,692,161 and 4,627,847 teach a leakage waste barrier for the edge of an absorbent hygienic article provided by coating a hot melt adhesive onto the edge area of a nonwoven sheet material. Depending on the actual type of application, this hot melt adhesive can also serve a constructive function, in combination with its function as a barrier, in that it can adhere the nonwoven to other materials of the hygienic article. The hot melt is to be coated in a conventional manner by slot nozzle coating, transfer coating, spray coating or other such methods. The above-mentioned U.S. patents indicate that the hot melt coating must have a minimum thickness of 25 μm, preferably at least 75 μm, so that a continuous closed barrier layer is achieved.

Conventional slot nozzle coatings on uneven substrates such as nonwovens are typically done by keeping the slot nozzle in permanent contact with the substrate such that the nozzle lies on the substrate during the coating. It is unproblematic to coat hot melt adhesives onto uneven substrates with slot nozzles or spray coating methods, provided that only a discontinuous coating is required such as for constructive applications wherein the coating weight of the hot melt ranges from about 3 g/m$^2$ to about 10 g/m$^2$. If, however, a continuous layer is to be created, this can only be done using these customary coating methods if the coating weight of the hot melt is greater than about 30 g/m$^2$.

Such high coating weights are expensive. Furthermore, direct coating with a slot nozzle provides substantial mechanical and thermal stresses on the coated substrates, especially since the slot nozzle is heated during coating. Therefore, very sensitive substrates such as nonwovens made of very fine or low melting point fibers can not always be coated with hotmelt from a slot nozzle in a customary manner without damaging the substrate. Such problems can not be overcome when coating with heated coating rollers or spray coating with heated airstreams. The high coating weights of this prior art lead to increased stiffness of the coated substrate, thus impairing the textile character.

Similar problems occur in the production of hygienic articles and in other areas, such as fabric production, wherein the resulting materials are required to exhibit liquid impermeability, especially body fluid impermeability, with textile character which is as unimpaired as possible. This is especially pertinent for improving the comfort of the user. Presently, in such technical fields, production methods utilizing preformed laminated films are preferred. Therefore, there remains a need for a non-contact method capable of producing a continuous coating layer having low coating weights.

SUMMARY OF THE INVENTION

The applicants have found a coating method that overcomes the aforementioned problems. The coating method employs a noncontact application wherein a thermoplastic composition is thermally made flowable and released from a coating device onto a substrate. The thermoplastic composition is thus coated onto the substrate without contact between said coating device and said substrate. Preferably, a liquid-impermeable, especially a body fluid impermeable, barrier wherein the textile character is not substantially impaired is produced. Since the method employs low coating weights of the thermoplastic composition, it eliminates the economic disadvantages of current methods as well as improves the tactile quality of the resulting article. Additionally, the method is suitable for coating a variety of heat sensitive materials. Preferably, the substrate is a "textile material" which in the context of this invention means not only a woven material made of yarn, but also any material made from fibers such as nonwoven, as well as nonwoven composites and the like, which materials play a major role in the area of hygienic article production. Since the coating device and substrate do not contact each other, the mechanical stresses on the substrate are much less than prior art methods.

For heat sensitive substrate, the thermoplastic composition is preferably coated at temperatures of less than about 160° C., more preferably less than about 125° C., and most preferably less than 110° C., to reduce the heat-induced stresses on the substrates being coated. This is advantageous for coating and mutually bonding thermally sensitive substrates.

The thermoplastic composition preferably exhibits certain rheological characteristics such that the complex viscosity at high shear rates (1,000 rad/sec) is less than about 500 poise and the complex viscosity at low shear rates (1 rad/sec) is between about 100 and about 1,000 poise. Some neat thermoplastic resins, such as typical film grade polyolefins, may be suitable for the method of the present invention. However, compounded hot melt adhesives are preferred due to the ability to independently control the visco-elastic properties, open time, etc. Compounded hot melts are advantageous to insure adequate adhesion to the carrier substrate or for delayed detackification of the coating after adherence to the substrate.

The resulting coating produced from said method is useful for a variety of applications wherein a consistent continuous coating is desired. Coating weights of less than 30 g/m$^2$ of the thermoplastic composition are preferred to reduce expenditure and improve the tactile quality of disposable hygienic articles. However, coating weights higher than 30 g/m$^2$ may be useful for other applications wherein reducing the mechanical and heat-induced stresses is of primary importance.

The resulting coating is preferable for producing a body fluid impermeable barrier layer in a disposable hygienic article having improved exterior tactile quality. The coating method is particularly advantageous for manufacturing as it employs fewer production steps than prior art coating methods. Improving productivity as well as reducing the coating weight mass per area results in coatings and corresponding articles that are less expensive than prior art.

The disposable article comprises at least one permeable substrate layer and at least one fluid impermeable barrier layer substantially adhered to the permeable substrate layer on at least one face, wherein the barrier layer comprises a thermoplastic compositions coated as a continuous film at an area weight of less than 30 g/m$^2$. Preferably, the barrier layer is produced from the coating method described herein. The permeable substrate is preferably a nonwoven web. However, paper, durable fabric, as well as any other material available as a roll good may be coated with this coating method. The permeable substrate may contribute significantly to the overall strength and integrity of the lamination. Preferably, the substrate exhibits sufficient strength such that it can not be torn easily by hand in either machine direction or in cross-direction.

This coating method is particularly useful for coating certain thermoplastic compositions that contribute desirable properties, yet are typically unsuitable for traditional extrusion die coating methods and can not be converted into a finished film.

DETAILED DESCRIPTION OF THE DRAWING

Figure 1:
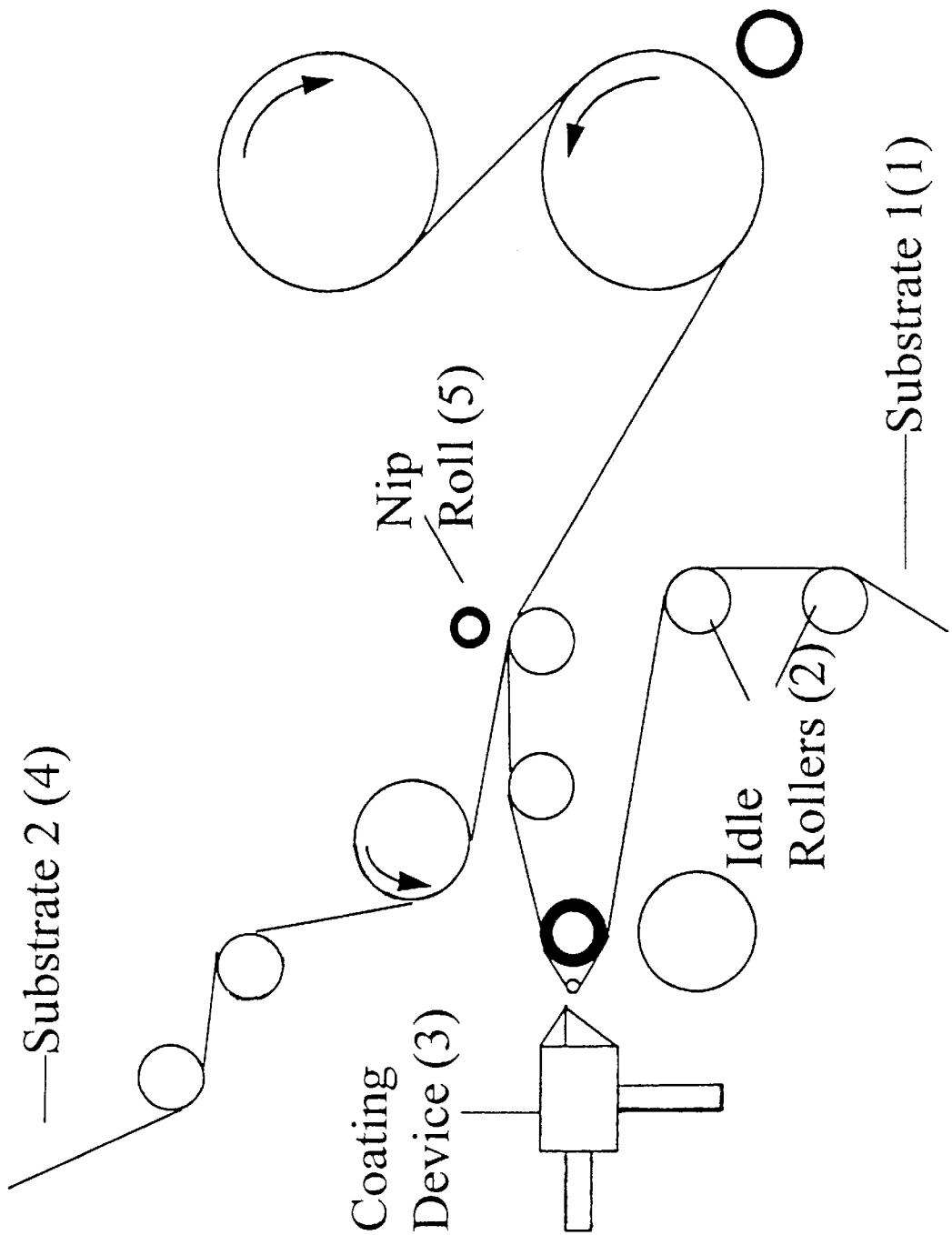
FIG. 1 depicts the method of the present invention wherein a continuous thermoplastic coating is formed and adhered to a carrier substrate.

Substrate 1 (1) is advanced by the drive rolls (6) past a series of idle rollers (2) to ensure the web is in proper alignment prior to approaching the coating device (3). The coating device is located at a distance most often ranging from about 0.5 mm to about 20 mm, depending on the properties of the thermoplastic composition being coated. Substrate 2 (4) is optionally adhered to the coated surface of Substrate 1 by means of a nip roll (5). When adherence to a second substrate is intended, it is often preferred to position the nip roll closer to the coating device at a distance of about 25 cm from the coating device. In the preferred embodiment, Substrate 1 is a nonwoven web and Substrate 2 may be any material present in a hygienic article such as an absorbent, elastomeric strands or webs, tissue, films, coverstock materials such as nonwoven or perforated polyethylene, as well as any material that is not necessarily in the form of a web such as superabsorbent polymer.

DETAILED DESCRIPTION OF THE INVENTION

In the method of the present invention, a melted hotmelt adhesive, preferably substantially air-free, is released from a coating or release device in such a way that it exits the device as a continuous film. A typical example for this is a slot nozzle, as it has previously been used for coating in direct contact with a substrate. Thus, melt coating devices which are already at hand can be reset for use according to the invention in that the slot nozzle is lifted off the substrate and is adjusted to have a suitable distance from the substrate.

When the viscous but flowable molten adhesive leaves the coating device, it does not contact the substrate immediately, but rather travels for a distance as a continuous coating film suspended above the substrate without touching either the device or the substrate. The distance between the coating device and the substrate ranges from about 0.5 mm to about 20 mm. It is possible that at suitable machine speed settings, and with specific adhesives or other coating materials, the distance can be even greater than 20 mm. The distance is largely dictated by the viscosity, flow properties such as shear thinning behavior, line speed and open time of the thermoplastic composition being coated. It is surmised that the thermoplastic composition builds sufficiently in viscosity and cohesive strength to the extent that any filaments or fibers present on the substrate surface cannot penetrate the coating, yet the thermoplastic composition is molten or soft enough to adequately adhere to the substrate.

It has been shown to be especially advantageous, that the coating later contacts the substrate in a substantially horizontal direction rather than in a vertical direction. To realize this advantage, a roller can be provided in the path of movement of the substrate to give the substrate a substantially vertical, upward direction, as the substrate passes the coating device. Additionally, the coating device, such as a slot nozzle, can be provided substantially horizontally beside the roller so that the coating travels from the side towards the surface of the substrate.

The diameter of the coating role is preferably about 15 mm to about 50 mm in diameter with the nozzle above the center of the coating roll such that the angle at which the thermoplastic coating contacts the substrate is less than about 60° C. as the substrate is moving away from the nozzle. The coating head is adjusted by one of ordinary skill in the art to optimize for even flow and distribution of the thermoplastic coating over the entire width of the application.

Thereafter, the sufficiently viscous coating contacts the substrate surface and adheres to the surface without deeply penetrating into the substrate. Particularly for coating thermoplastic compositions that are relatively tack free upon cooling, there is a distinct interface between the coating and the substrate which is evident by the ability to remove the coating as a continuous film from the substrate. This interface is also present when a tacky thermoplastic composition is employed. However, in this instance since the coating and the substrate are inseparable, the interface is not quite so evident. When the substrate is preferably a textile material such as a nonwoven, the thus produced material comprises the textile substrate layer and a coating, preferably a hotmelt barrier layer. If the thermoplastic coating is of such a composition that it substantially detackifies after sufficient cooling, the laminate of the coated substrate, thus formed, can be rolled up and stored. The laminate can then be used at some later time e.g. as a body fluid impermeable backsheet having improved tactile quality in a disposable hygienic article. The laminate can be bonded by any suitable bonding technique including ultrasonic bonding, heat welding, or more commonly adhesive bonding.

Preferably, the coating of the barrier layer is done "inline" immediately before any further processing of the thus produced coated textile laminate. In such a case, the surface of the barrier layer which is pointing away from the substrate and is still sufficiently tacky can be used for a constructive adhesion step and therefore can also serve to bond the coated textile material to other elements of a hygienic article. Other elements that could be simultaneously bonded in this manner during the formation of the barrier layer include absorbent, elastomeric strands or webs, tissue, films, coverstock materials such as nonwoven or perforated films, as well as any other material that is not necessarily in the form of a web such as superabsorbent polymer. This method has been found to be particularly advantageous for bonding porous web including book and loop fastening webs such as Velcro®.

Since the hot melt coating can be provided at extremely low temperatures, materials can also be provided with barrier layers which are too sensitive mechanically and/or thermally for customary coating methods. Such sensitive materials include low gauge polyethylene materials, low basis weight nonwovens and the like.

A substantial advantage of the invention is that continuous, sufficiently impermeable barrier layers can be made from hotmelts at very low coating weights. Even with customary commercially available hotmelts, closed barrier layers can be produced at coating weight of not more than 30 g/m², and generally, it is easily possible to achieve coating weights between 10 g/m² and 20 g/m² and most preferably less than 10 g/m². As previously stated, the prior art coating of hot melts according to customary methods for forming edge leakage barriers, as in U.S. Pat. No. 4,692,161, requires area weights of about 70 g/m² to create the preferred film thickness of around 75 µm. At thickness of 25 µm, the suggested minimum according to this art, the contact-coated layer is perforated by substrate fiber, and is not closed.

The very thin barrier layers which can be produced according to the invention do not only contribute to the economical advantages of the inventive method, but also make it possible to achieve a very much reduced stiffness of the material, which thus comes much closer, in its properties, to a textile material which is not provided with a barrier layer at all. The reduced stiffness is achieved not only by the reduced coating weight thickness but also due to the ability to coat thermoplastic materials that are typically unsuitable for traditional extrusion die coating methods and can not be converted into a finished film. The film itself, formed from this method typically does not exhibit sufficient strength unless it is supported by the substrate upon which it is coated.

The Thermoplastic Composition

As previously mentioned, uncompounded thermoplastic materials such as polyolefins, especially polyethylene, polypropylene, amorphous polyolefins such as Vestoplast 703® (Hüls), metallocene polyolefins, and the like, may be suitable thermoplastic materials for the coating method of the present invention. However, hot melt adhesives are preferred due to the ability to independently tailor the visco-elastic properties, open time, tack, and various other properties. Hot melt adhesives commonly have viscosity profiles that allow for processing at very low temperatures. Typical hotmelts are fluid enough for such processing at temperatures ranging from about 60° C. to 110° C.

More preferably, the thermoplastic composition exhibits certain rheological characteristics such that a continuous, body fluid impermeable coating can be produced at coating weights of less than about 30 g/m². In general, the Theological properties preferably fall within a rheological window wherein the complex viscosity at high shear rates (1,000 rad/sec) is less than about 500 poise and the complex viscosity at low shear rates (<1 rad/sec) is between about 100 and about 1,000 poise. In other words, preferable thermoplastic compositions exhibit Newtonian regions at low shear rates and shear thinning at higher shear rates. Thermoplastic compositions having wide windows of application are those in which the composition exhibits the appropriate rheological properties at a variety of application settings, particularly low temperatures. Narrow application windows are those in which the rheological parameters are only met under very specific conditions. Amorphous polyolefins based hot melt adhesives such as Lunatack® D-8370 (H.B. Fuller Company) tend to exhibit relatively wide application windows whereas block copolymer based hot melt adhesives tend to exhibit narrow application windows.

Data generated that supports this rheological window is depicted in Table I. The test procedures used to determine the rheological data are described in detail hereinafter. The applicants surmise that the high shear rate data relates to the processing conditions at the slot die exit. A composition with too high of a complex viscosity at 1,000 radians/sec would require excessive pump pressure to exit the coating device. A die with a shim gap larger than 3 mm could be used to process these materials but a higher coating weight may result.

The low shear rate data relates to the settling of the coating on the substrate during the time it is suspended above the substrate. If the low shear value is too high, the coating may not adhere adequately to the substrate and/or the thermoplastic composition builds up at the nozzle causing a streaked, discontinuous coating. If the low shear viscosity is too low, the coating may seep into the substrate, causing poor barrier properties.

Extensional viscosity, which was not measured can also strongly influence the melt strength. Higher levels of branching or the addition of a small concentration of a high molecular weight material can strongly influence the melt strength. More preferred are compositions that meet the target rheological parameters at low application temperatures of less than about 160° C., more preferably less than about 125° C. and most preferably less than about 110° C.

Accordingly, many known hot melt adhesive compositions are well suited for use in the coating method of this invention. Hot melt adhesives typically comprise at least one thermoplastic polymer, at least one plasticizer and at least one tackifying resin. Preferably, such suitable hotmelts comprise up to 40% by weight of thermoplastic polymer, up to 40% by weight of a plasticizer and up to 70% by weight of tackifying resin.

With respect to the thermoplastic polymer, atactic polyalphaolefins such as Vestoplast® 708 (Hüls) and synthetic rubbers such as S-EB-S block copolymers have been found to be especially suited, particularly those as used in hot melt adhesives such as Lunatack® D-3964 (H.B. Fuller). Further, however, other thermoplastic polymers are suitable, such as ethylenic copolymers including ethylene-vinyl acetate, ethylene-methyl acrylate, copolymers or other synthetic rubbers as available in commerce under the tradenames Kraton®, Solprene®, and Stereon®.

In the case of polyolefins and ethylenic copolymers, polymer concentrations as high as 100% may be suitable. It should be noted that compositions useful for traditional extrusion die coating are typically not suitable uncompounded for the coating method described herein. Such commercially available neat resins such as polypropylene and polyethylene do not have a sufficiently low enough complex viscosity at low temperatures, preferably less than 160° C., to be coated in this manner. Furthermore, a single unimodal polymer of sufficiently low enough complex viscosity is typically high in density, greater than about 0.90 g/cm$^2$. Due to being highly crystalline in nature, such neat polymers do not possess the proper balance of visco-elastic properties to produce fluid-impermeable coatings at low coating weights.

Plasticizers and tackifying resins used in hot melt adhesives are known. Oils such as naphthenic oils are preferred plasticizers. As for tackifying resins, those resins already known for such purposes are generally suitable, especially hydrocarbon resins, ester resins and other such compatible resins. The components are mixed and processed in a known manner to prepare the hotmelts which can be used according to this invention.

With suitable hot melts, such as those described in DE-A-41 21 716, it is also possible to make materials which are impermeable to liquid water, yet water vapor permeable rendering the coating "breathable".

In addition to commonly known hot melt adhesives, thermoplastic compositions comprising a water soluble, saline (body fluid) insoluble copolyester such as Eastman AQ 1350®, commercially available from Eastman, are also particularly useful for creating barrier films that are impervious to body fluid, yet readily water soluble. This feature is of particular interest for creating flushable and compostable disposable hygienic products. Furthermore, there may be applications wherein water permeability is desired. Accordingly, this coating method may also be suitable for coating water permeable, water soluble and/or biodegradable thermoplastic materials.

Hereinafter, the invention will be further depicted by the following nonlimiting examples.

EMBODIMENT EXAMPLE 1

Several hot melts which slightly differ from each other in composition were formulated in the following composition ranges:

20–25% naphthenic oil
30–40% atactic polyolefin(s)
35–45% hydrocarbon resin

EMBODIMENT EXAMPLE 2

Several hot melts were formulated within the following range limits:

15–20% SIS-block copolymer
15–25% naphthenic oil
50–65% ester resin

EMBODIMENT EXAMPLE 3

As a commercially available hot melt adhesive, the "Lunatack D 8370" product was used, which is available from H. B. Fuller GmbH. This is a hot melt adhesive comprising about 35% polyolefin, about 40% hydrocarbon resin with a cyclopentadiene component, about 15% polyisobutylene and about 10% naphthenic oil.

EXAMPLES 4–28

Table 1 depicts rheological data on examples 4 through 16 and examples 18 through 28. Column 2 of Table 1 depicts the reference temperature for the Theological parameters as well as the coating application temperature for each sample. Table 2 and Table 3 depict the chemical description of examples 4 through 28 as well as the coating parameters for those examples in which a continuous coating resulted. A consistent continuous coating was not able to be produced with Samples 4 through 9 at the temperature indicated in Column 2. The applicants surmise that the inability to produce a continuous coating is due to the complex viscosity being greater than about 1000 poise at about 1 rad/sec. By comparing examples 5 with 14 and 4 with 10, the complex viscosity at 1 rad/sec can be forced into the rheological window by increasing the temperature. By comparing example 7 with 16, the applicants have demonstrated the relatively narrow rheological window of Lunatack® D-3964. At 90° C. D-3964 exhibits too high of a complex viscosity at 1 rad/sec. At 110° C., D-3964 exhibits too low of a complex viscosity at 1 rad/sec, causing the material to soak into the substrate. The applicants surmise a temperature exists between 90° C. and 110° C. wherein D-3964 would produce a continuous coating. However, a thermoplastic composition exhibiting such a narrow rheological window would have little chance of commercial success.

Example 14 exhibits the utility of blending a thermoplastic composition that does not meet the rheological window with another material such that the resulting composition is useful for producing a continuous coating. In this particular example, since D-3964 exhibits too low of a complex viscosity at 1 rad/sec to produce a continuous coating at a coat weight of about 10 g/m$^2$, it is blended with a material to raise the complex viscosity at 1 rad/sec and to improve the shear thinning properties such that the blend exhibits the preferable rheological properties. Alternatively, the low complex viscosity at 1 rad/sec is unproblematic for coating weights of about 20 g/m$^2$ and higher as illustrated by examples 24 through 26.

Examples exhibiting too high of a complex viscosity at 1 rad/sec, such as examples 4 through 9 can be blended with compatible materials to lower the complex viscosity such that the blended material may be coated at the preferable application temperature of less than 160° C.

The thermoplastic composition of examples 18 and 19 is particularly preferred since the resulting coating demonstrated no change in water penetration after being aged for 3 days at 60° C.

The compositions of experimental samples D573BD7 and D573BD8 are depicted below.

| Parts (pph) | Tradename | Chemical Description |
|---|---|---|
| | Experimental Sample D573BD7: | |
| 33.0 | LOTRYL 35 BA 40 (Elf Atochem) | Ethylene n-butyl acrylate copolymer |
| 24.7 | ECR-179 A (Exxon) | Tackifying resin |
| 20.0 | REGALITE R 125 (Hercules) | Tackifying resin |
| 15.0 | PETRBRAS K 521 (A. Kochen, GmbH) | Wax |
| 5.0 | CATENEX P941 (Shell) | Plasticizing oil |
| .15 | IRGANOX 1010 (Ciba Geigy) | Antioxidant |
| .15 | Irganox PS 800 (Ciba Geigy) | Antioxidant |
| | Experimental Sample D573BD8: | |
| 33.0 | ESCORENE UL 02528 | Ethylene vinyl-acetate |
| 24.7 | ECR-179 A (Exxon) | Tackifying resin |
| 20.0 | REGALITE R 125 (Hercules) | Tackifying resin |
| 15.0 | PETROBRAS K 521 (A. Kochen, GmbH) | Wax |
| 5.0 | CATENEX P941 (Shell) | Plasticizing oil |
| .15 | IRGANOX 1010 (Ciba Geigy) | Antioxidant |
| .15 | IRGANOX PS 800 (Ciba Geigy) | Antioxidant |

Test Methods

Coating Procedure

The hot melts according to embodiment examples 1 through 3 were placed in a customary processing machine provided with a slot nozzle such as Nordson EP 51. The slot nozzle was provided horizontally facing a roller over which a 23 g/m² basis weight spunbond polypropylene nonwoven (Corovin®A23A40 Corosoft-Plus, Corovin GmgH) was led in an upward direction. The distance between the slot nozzle and the substrate was 2 mm, at a nozzle slot length of 70 mm. The web speed of the nonwoven was 25 m/min. At a system pressure of about 53 bar and a release temperature of the hot melt of approximately 100° C., the hot melt was coated onto the substrate, where it formed a closed barrier layer. Immediately thereafter, the thus coated substrate was adhered to a customary absorptive body (tissue). In each case, a reliable adhesive bond between substrate and tissue was provided, and in each case, the hot melt barrier layer formed between the tissue and the substrate was found to be completely liquid-impermeable. Processing was without any problems. The coating weight was an average of 21 g/m². At corresponding fine adjustment of release temperature of hot melt, system pressure, distance between slot nozzle and substrate, machine speed etc. etc., it was systematically possible to form water-tight closed barrier layers at area weights of less than 20 g/m² on this substrate.

Examples 4 through 28 were coated in a similar manner as examples 1–3 with the exception that the coating was not adhered to tissue. The application conditions and rheological data of the adhesive compositions are depicted in Table 1. A system back pressure ranging from about 40 to about 65 bar was obtained during coating of examples 10 through 28.

Rheological Testing

The rheological data was generated from a dynamic mechanical spectrometer such as a Rheometric Scientific RDS 7700 (10,000 g/cm transducer, 10 g/cm–<10,000 g/cm torque). A master curve of G'(shear storage modulus), G" (shear loss modulus) and complex viscosity as a function of frequency was obtained through time temperature superposition. During testing the sample was loaded at the upper test temperature between 50 mm diameter parallel plate discs with a 1 to 2 mm gap. After allowing the sample temperature to stabilize for at least about 10 minutes, a frequency sweep was performed from about 0.1 to about 100 radians per second. Upon the completion of the frequency sweep, the sample temperature was lowered to the next temperature and the procedure repeated. The strain amplitude was adjusted to improve the resolution and ranged from about 20% to about 40%. After the frequency sweep was completed at the final, lowest temperature, time-temperature superposition was used to overlay the data into a single master curve at the application temperature. If the actual coating temperature was not one of the actual temperatures tested, the Williams, Landel, Ferry (WLF) (Ferry, J. D. *Viscoelastic Properties of Polymers*, 3rd Ed., Wiley: NY, 1980) equation was used to obtain the master curve.

Time-temperature superposition can be applied for amorphous compositions as well as for crystalline compositions for temperatures above the melt temperature. Capillary rheometry could be used to measure the viscosity at high shear rates.

Water permeability

The coated nonwoven was tested according to EDANA 160.0-89 "Wet Barrier" test method. The samples were conditioned for 24 hours at 50%±-2% relative humidity, 23° C.±-2° C. prior to testing. The samples were fixed (hot melt surface facing the water) to a cylindrical vessel, fitted with a bolted ring for clamping samples with a circular test area. The water pressure was increased recording the values the first drop (rather than the third as described in ERT 120.1-80) appeared on the surface of the nonwoven.

TABLE 1

| Example | Temp. (°C.) | Complex Viscosity 1 rad/sec (poise) | Complex Viscosity 10³ rad/sec (poise) | G' 1 rad/sec (dynes/cm²) | Crossover Frequency (rad/sec) | Tan delta @ 1 rad/sec | Slope = Visc @ 1/1000 rad/sec | Continuous Coating Formed yes/no |
|---|---|---|---|---|---|---|---|---|
| 4 | 125 | 15000 | 100 | 10000 | 1 | 1 | 150 | no |
| 5 | 90 | 10000 | 300 | 3000 | 300 | 3 | 33 | no |
| 6 | 120 | 4500 | 1500 | 300 | 1000 | 30 | 4.5 | no |
| 7 | 90 | 3000 | 100 | 400 | 50 | 7 | 30 | not tested |
| 8 | 110 | 2000 | 500 | 700 | 10000 | 3 | 4 | no |
| 9 | 140 | 1000 | 500 | 50 | >1000 | 70 | 2 | no |
| 10 | 160 | 200 | 200 | 5 | >1000 | 4 | 1.25 | yes |
| 11 | 125 | 800 | 100 | 5000 | 20 | 1 | 8 | yes |
| 12 | 125 | 800 | 100 | 100 | 1000 | 10 | 8 | yes |
| 13 | 125 | 300 | 50 | 200 | 1 | 1 | 6 | not tested |
| 14 | 110 | 300 | 50 | 20 | 7000 | 20 | 6 | yes |
| 15 | 128 | 100 | 80 | 10 | 1000 | 10 | 1.25 | yes |
| 16 & 24–26 | 110 | 100 | 3.5 | 8 | 100 | 25 | 28 | no |
| 18 | 130 | 350 | 90 | 40 | >1000 | 10 | 4 | yes |
| 19 | 110 | 800 | 130 | 130 | 1000 | 8 | 6 | yes |

TABLE 1-continued

| Example | Temp. (°C.) | Complex Viscosity 1 rad/sec (poise) | Complex Viscosity $10^3$ rad/sec (poise) | G' 1 rad/sec (dynes/cm$^2$) | Crossover Frequency (rad/sec) | Tan delta @ 1 rad/sec | Slope = Visc @ 1/1000 rad/sec | Continuous Coating Formed yes/no |
|---|---|---|---|---|---|---|---|---|
| 20 | 140 | 120 | 60 | 1 | >1000 | 50 | 2 | yes |
| 21 | 110 | 500 | 200 | 20 | 1000 | 20 | 2.5 | yes |
| 22 & 23 | 130 | 250 | 120 | 10 | >1000 | 30 | 2 | yes |
| 27 & 28 | 120 | 120 | 60 | 1 | 1100 | 100 | 2 | yes |

TABLE 2

| Example | Tradename(s) | Chemical Description | Coating Weight (GSM) | Speed M/MIN | Permeability cm$^3$ of H$_2$O pressure |
|---|---|---|---|---|---|
| 4 | 347-BD-19 (H. B. Fuller) | atactic polyolefin hotmelt adhesive (HMA) | | | |
| 5 | D-3964 + 10% Vestoplast ® 750 | SEBS block copolymer/hydrocarbon resin/napthenic oil HMA + atactic polyolefin | | | |
| 6 | Eastman AQ ® 1350 | water dispersible copolyester (WO 95/18191) | | | |
| 7 | D-3964 | SEBS block copolymer/hydrocarbon resin/napthenic oil HMA | | | |
| 8 | NP-2085 (HBF) | urethane | | | |
| 9 | Eastman AQ ® 1350 | see Example 6 | | | |
| 10 | Eastman AQ ® 1350 | see Example 6 | | | |
| 11 | Vestoplast ® 703 (Huls) | atactic polyolefin | 22 | 30 | — |
| 12 | 347-BD-33 (HBF) | atactic polyolefin HMA | 10 | 30 | 100 |
| 13 | Vestoplast ® 703 + 10% Paraflint H4 | atactic polyolefin + Fischer Tropsch wax | | | |
| 14 | D-3964 + 10% Vestoplast ® 750 | SEBS block copolymer/hydrocarbon resin/napthenic oil HMA + atactic polyolefin | 9–11 | 34 | 50 |
| 15 | D-8370 | atactic polyolefin HMA | 12 | 30 | 46 |
| 16 | D-3964 | see Example 7 | 8 | 30 | — |
| 17 | Vestoplast ® 750 + 10% Wax | see Example 13 | 15–16 | 30 | — |

TABLE 3

| Example | Tradename(s) | Chemical Description Coating Temperature | Coating Weight (GSM) | Speed M/MIN | Permeability cm$^3$ of H$_2$O pressure |
|---|---|---|---|---|---|
| 18 | Lunatack ® D-9105 (H. B. Fuller) | atactic polyolefin HMA 130° C. | 7–8 | 200 | 80 |
| 19 | Lunatack ® D-9105 | atactic polyolefin HMA 110° C. | 10–11 | 50 | 230 |
| 20 | Experimental Sample D573BD7 | ethylene n-butyl acrylate copolymer HMA 140° C. | 18 | 200 | 20 |
| 21 | Experimental Sample D573BD8 | ethylene vinyl-acetate copolymer HMA 110° C. | 6–8 | 200 | not tested |
| 22 | Experimental Sample D573BD8 | ethylene vinyl-acetate copolymer HMA 130° C. | 38 | 30 | 220 |
| 23 | Experimental Sample D573BD8 | ethylene vinyl-acetate copolymer HMA 130° C. | 15–16 | 100 | 20 |
| 24 | Lunatack ® D-3964 (H. B. Fuller) | see Example 7 110° C. | 62 | 30 | 300 |
| 25 | Lunatack ® D-3964 | see Example 7 110° C. | 27 | 30 | 20 |
| 26 | Lunatack ® D-3964 | see Example 7 110° C. | 20 | 150 | not tested |
| 27 | Experimental Sample D181BD18ZP | SIS block copolymer HMA 120° C. | 27 | 100 | 20 |
| 28 | Experimental Sample D-181BD18ZP | SIS Block Copolymer HMA 120° C. | 12 | 200 | not tested |

What is claimed is:

1. A disposable article comprising at least one permeable substrate layer and at least one fluid impermeable barrier layer, said barrier layer having an area weight of less than 20 g/m$^2$ substantially adhered to the permeable substrate layer on at least one face, wherein said barrier layer comprises a hot melt adhesive coated as a continuous film.

2. The disposable article of claim 1, wherein the article further comprises at least one absorbent material.

3. The disposable article of claim 1, wherein the barrier layer is moisture-vapor permeable.

4. The disposable article of claim 1, wherein the permeable substrate layer is a textile material.

5. The article of claim 1, wherein the hot melt adhesive comprises a thermoplastic composition wherein the complex viscosity of the thermoplastic composition at the coating temperature is less than about 500 poise at about 1,000 radians/sec.

6. The article of claim 5, wherein the hot melt adhesive comprises at least one polymer selected from the group consisting of block copolymers, water dispersible copolyesters, ethylenic copolymers, polyolefins, metallocene polyolefins, atactic polyolefins and mixtures thereof.

7. The article of claim 5, wherein the coating temperature is less than about 160° C.

8. The article of claim 5 wherein the thermoplastic composition is shear thinning.

9. The article of claim 1, wherein the hot melt adhesive comprises a thermoplastic composition wherein the complex viscosity of the thermoplastic composition at the coating temperature ranges from about 100 poise to 1,000 poise at about 1 radian/sec.

10. The article of claim 9, wherein the hot melt adhesive comprises at least one polymer selected from the group consisting of block copolymers, water dispersible copolyesters, ethylenic copolymers, polyolefins, metallocene polyolefins, atactic polyolefins and mixtures thereof.

11. The article of claim 9, wherein the coating temperature is less than about 160° C.

12. The article of claim 1, wherein the hot melt adhesive forming the barrier layer is subsequently bonded to at least one other material.

13. The article of claim 1, wherein the hot melt adhesive is bonded to at least one other material inline after coating of the thermoplastic composition.

14. The article of claim 1, wherein the area weight of the barrier layer is less than 10 g/m$^2$.

15. An article comprising a permeable substrate and a body fluid impermeable barrier layer substantially adhered to the permeable substrate on at least one face, wherein the area weight of said barrier layer is less than about 10 g/m$^2$.

16. An article comprising a body fluid impermeable barrier wherein said barrier layer is a coating comprising a thermoplastic composition wherein the complex viscosity at the coating temperature of said composition is less than about 500 poise at about 1,000 radians/second and ranges from about 100 to about 1000 poise at 1 radian/sec, wherein said composition is coated at an area weight of less than about 20 g/m$^2$.

17. The article of claim 16 wherein the thermoplastic composition is shear thinning.

18. An article comprising a body fluid permeable barrier layer, said barrier layer formed by a method comprising the steps of;
   a) providing a flowable thermoplastic composition having a complex viscosity at the coating temperature of less than about 500 poise at about 1,000 radians/second and ranging from about 100 to about 1000 poise at 1 radian/sec;
   b) providing a moving substrate:
   c) dispensing said thermoplastic composition as a continuous film from a coating device;
   d) suspending said film between said coating device and said substrate;
   e) contacting said film with said substrate.

19. The article of claim 18 wherein the thermoplastic composition is shear thinning.

20. A disposable article comprising a permeable substrate layer and a fluid impermeable barrier layer substantially adhered to the permeable substrate layer on at least one face, wherein said barrier layer consists essentially of a single layer of a hot melt adhesive coated as a continuous film having a film thickness of less than 75 microns.

* * * * *